United States Patent
Tonotsuka et al.

(10) Patent No.: US 10,058,295 B2
(45) Date of Patent: Aug. 28, 2018

(54) X-RAY IMAGING APPARATUS

(71) Applicant: Toshiba Medical Systems Corporation, Otawara-shi (JP)

(72) Inventors: Hiroki Tonotsuka, Otawara (JP); Shunichiro Nishigaki, Otawara (JP); Seiichi Nishizuka, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 382 days.

(21) Appl. No.: 14/582,511

(22) Filed: Dec. 24, 2014

(65) Prior Publication Data

US 2015/0117609 A1 Apr. 30, 2015

Related U.S. Application Data

(63) Continuation of application No. PCT/JP2013/071269, filed on Aug. 6, 2013.

(30) Foreign Application Priority Data

Aug. 6, 2012 (JP) .................................. 2012-174255

(51) Int. Cl.
*A61B 6/02* (2006.01)
*A61B 6/04* (2006.01)
*A61B 6/00* (2006.01)

(52) U.S. Cl.
CPC .......... *A61B 6/4476* (2013.01); *A61B 6/4429* (2013.01); *A61B 6/4458* (2013.01);
(Continued)

(58) Field of Classification Search
CPC .... A61B 6/00; A61B 6/02; A61B 6/44; A61B 6/4411; A61B 6/4429; A61B 6/4458;
(Continued)

(56) References Cited

U.S. PATENT DOCUMENTS 5,521,957 A * 5/1996 Hansen ................ A61B 6/4405
378/196
6,200,024 B1 * 3/2001 Negrelli ............... A61B 6/4233
378/196
(Continued)

FOREIGN PATENT DOCUMENTS

CN 101801271 A 8/2010
JP 01-148237 A 6/1989
(Continued)

OTHER PUBLICATIONS

Combined Office Action and Search Report dated Jul. 7, 2015 in Chinese Patent Application No. 201380003266.5 with English translation of category of cited documents.
(Continued)

*Primary Examiner* — Anastasia Midkiff
(74) *Attorney, Agent, or Firm* — Oblon, McClelland, Maier & Neustadt, L.L.P.

(57) ABSTRACT

According to one embodiment of an X-ray imaging system, a column, including a first sub column, a second sub column, a third sub column, a first connector, and a second connector, supports an X-ray tube. The first connector connects the second sub column to the first sub column and includes a first rotation axis parallel to a short axis of a tabletop. The second connector connects the third sub column to the second sub column and includes a second rotation axis perpendicular to the first rotation axis and a central axis of the second sub column. The third sub column supports the X-ray tube.

9 Claims, 6 Drawing Sheets

(52) U.S. Cl.
CPC .............. *A61B 6/587* (2013.01); *A61B 6/588* (2013.01); *A61B 6/589* (2013.01); *A61B 6/0407* (2013.01); *A61B 6/44* (2013.01); *A61B 6/4411* (2013.01); *A61B 6/4452* (2013.01); *A61B 2560/0443* (2013.01)

(58) Field of Classification Search
CPC ....... A61B 6/4473; A61B 6/04; A61B 6/0407; A61B 6/58; A61B 6/587–6/589; A61B 2560/00; A61B 2560/02; A61B 2560/04; A61B 2560/0443; A61B 2576/00; A61B 6/447; A61B 2576/006; H05G 1/00; H05G 1/02; G01T 7/00; H01J 23/12; G03B 42/04; G03B 42/047
See application file for complete search history.

(56) References Cited

U.S. PATENT DOCUMENTS

| | | | | |
|---|---|---|---|---|
| 6,582,121 B2* | 6/2003 | Crain | ..................... | A61B 6/107 378/189 |
| 7,832,927 B2* | 11/2010 | Dyreby | ................ | A61B 6/4464 378/194 |
| 7,988,357 B2* | 8/2011 | Hornung | .............. | A61B 6/4233 378/197 |
| 8,794,832 B2* | 8/2014 | Noda | ................... | A61B 6/4441 378/193 |
| 2001/0022833 A1* | 9/2001 | Kobayashi | ............. | G03B 42/02 378/177 |
| 2003/0112926 A1* | 6/2003 | Atzinger | .............. | A61B 6/4233 378/196 |
| 2004/0008820 A1* | 1/2004 | Schmitt | ................ | A61B 6/4441 378/193 |
| 2013/0083898 A1* | 4/2013 | Tajima | ................. | A61B 6/4283 378/97 |
| 2015/0117603 A1* | 4/2015 | Keeve | .................. | A61B 6/0407 378/62 |

FOREIGN PATENT DOCUMENTS

| | | | |
|---|---|---|---|
| JP | 04-371143 A | 12/1992 | |
| JP | 2000-093413 A | 4/2000 | |
| JP | 2001-340322 A | 12/2001 | |
| JP | 2002-058664 A | 2/2002 | |
| WO | WO 2013135888 A2 * | 9/2013 | .......... A61B 6/0407 |

OTHER PUBLICATIONS

International Search Report dated Sep. 3, 2013 for PCT/JP2013/071269 filed Aug. 6, 2013 with English Translation.
International Written Opinion dated Sep. 3, 2013 for PCT/JP2013/071269 filed Aug. 6, 2013.
International Preliminary Report on Patentability and Written Opinion dated Feb. 19, 2015 in PCT/JP2013/071269 (English translation only).

* cited by examiner

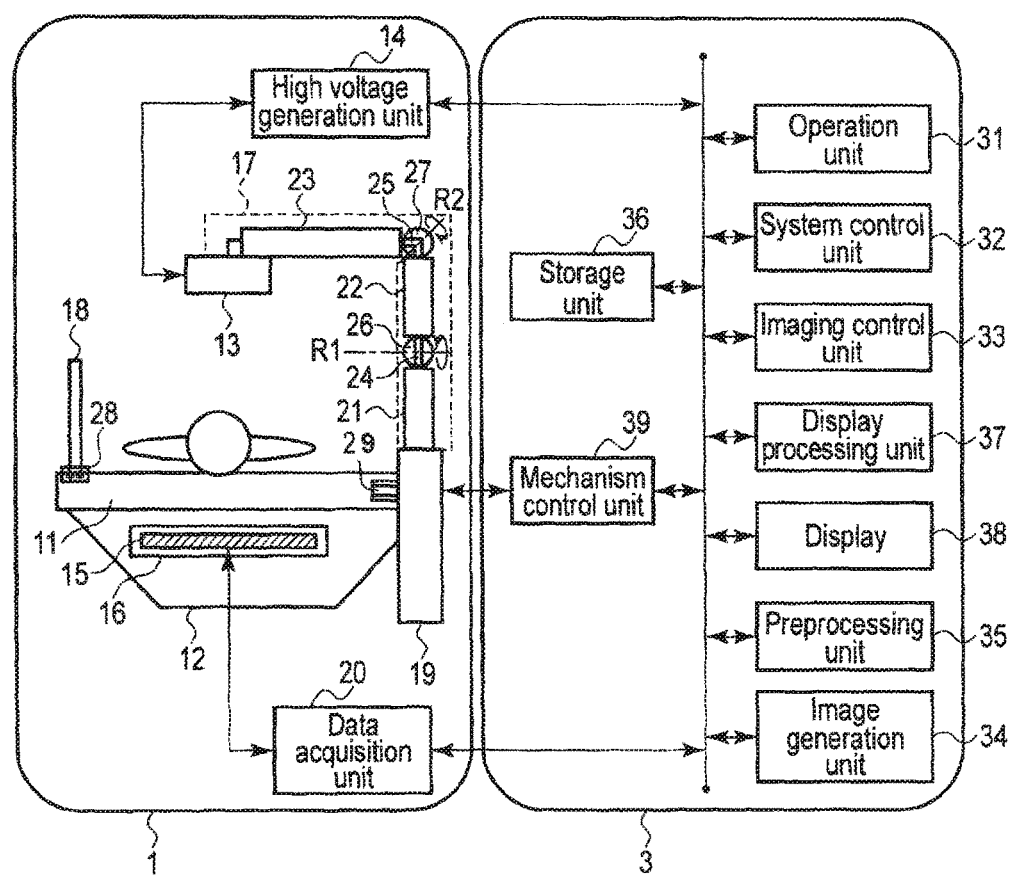
F I G. 1

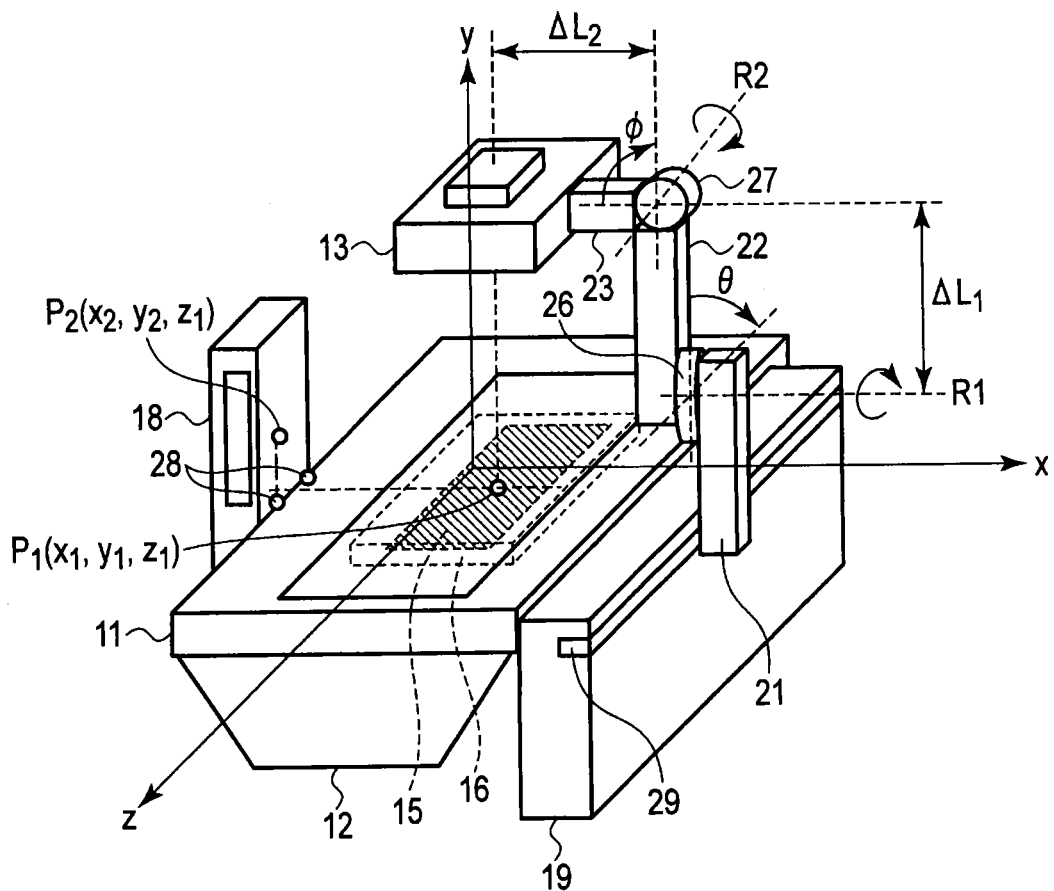
F I G. 2

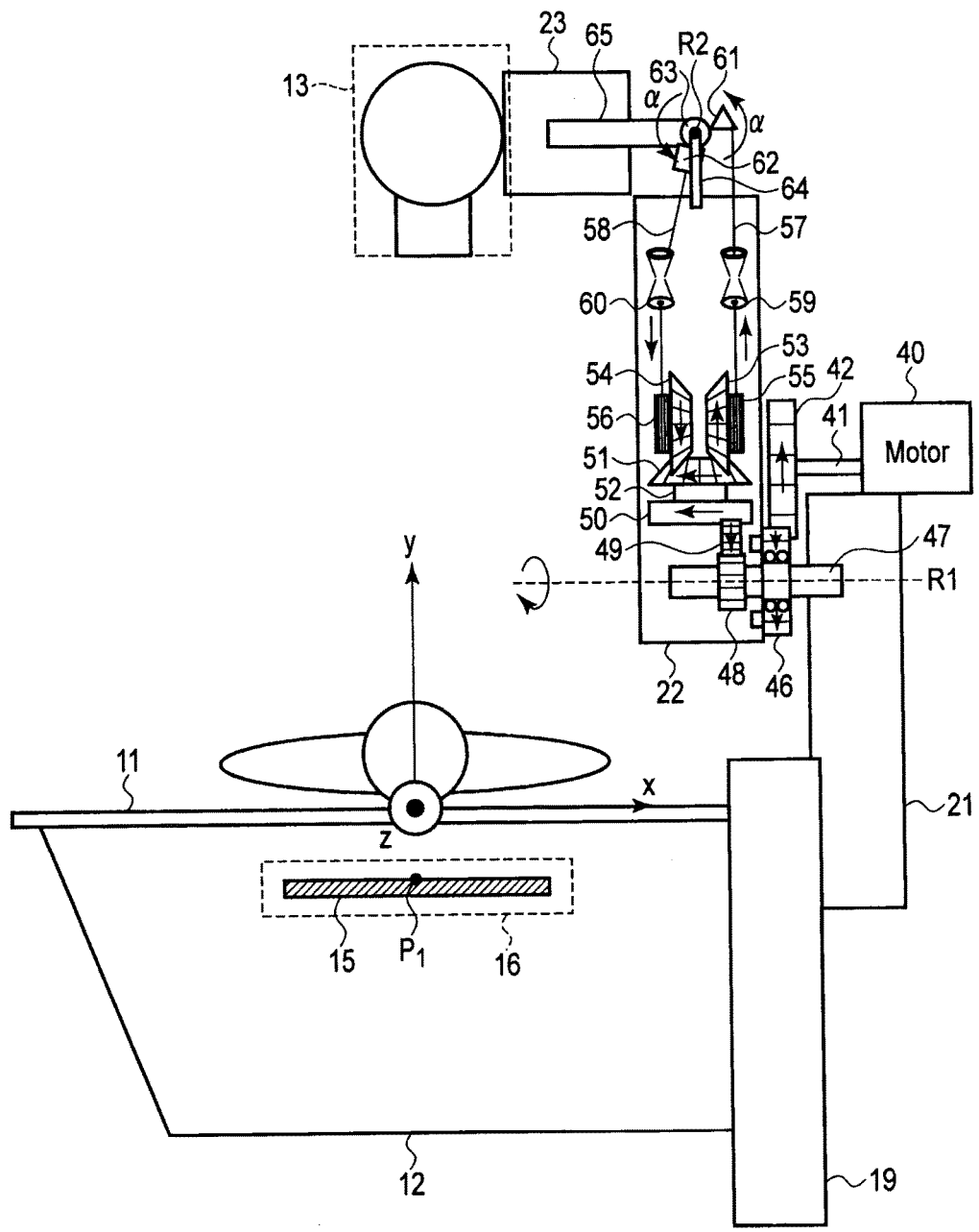
F I G. 6

X-RAY IMAGING APPARATUS

CROSS-REFERENCE TO RELATED APPLICATIONS

This application is a Continuation application of PCT Application NO. PCT/JP2013/071269, filed Aug. 6, 2013 and based upon and claims the benefit of priority from the Japanese Patent Application NO. 2012-174255, filed Aug. 6, 2012, the entire contents of all of which are incorporated herein by reference.

FIELD

Embodiments described herein relate generally to an X-ray imaging apparatus.

BACKGROUND

An X-ray imaging apparatus is an apparatus which provides medical information about a subject in the form of an image based on the intensity of X-rays transmitted through the object and plays an important role in medical activities such as diagnosis and medical treatment. Many types of X-ray imaging apparatuses customized for different applications have appeared on the market to cope with a wide variety of medical activities. Among these apparatuses, a general X-ray imaging apparatus including a table can be provided at low initial cost and in a small installation space as compared with an X-ray imaging apparatus including a C-arm, and hence is introduced into relatively small hospitals and medical facilities and widely used. However, an X-ray imaging apparatus is designed to cope with only imaging (frontal imaging) from a direction facing the tabletop surface of the table. If, therefore, the operator wants to perform imaging (lateral imaging) from a direction parallel to the tabletop surface of the table with respect to an ROI (Region Of Interest) of a subject as well as frontal imaging, the object needs to incline his/her body on the tabletop. The action of inclining the body is a large burden for an elderly person. In addition, when the object inclines his/her body, the positions of the organs change from those at the time of frontal imaging. This makes it impossible to compare a captured frontal image with a captured lateral image under the same conditions. This may result in inability to perform proper diagnosis.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 1 is a view showing the arrangement of an X-ray imaging apparatus according to an embodiment.

FIG. 2 is a perspective view showing the posture of a gantry at the time of frontal imaging by the X-ray imaging apparatus according to this embodiment.

FIG. 6 is a view showing the operating direction of each mechanical portion for shifting from the posture for lateral imaging to the posture for frontal imaging.

DETAILED DESCRIPTION

Figure 3:
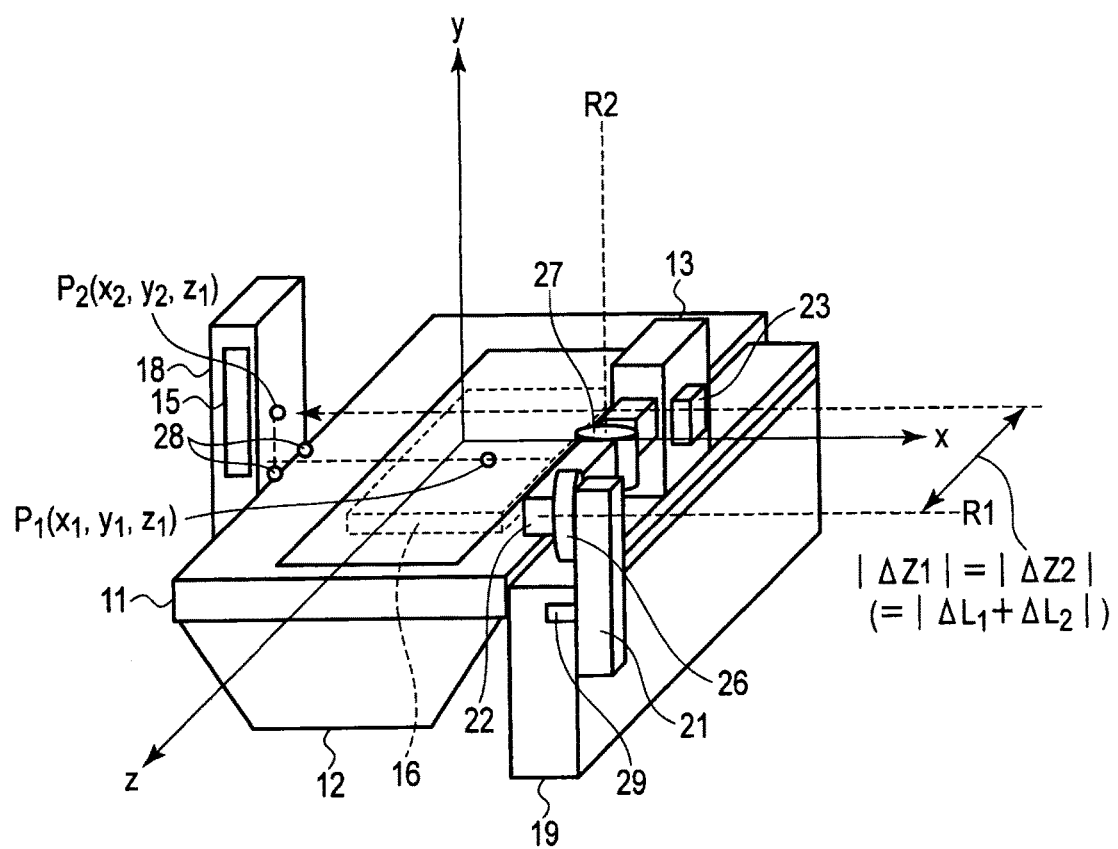
FIG. 3 is a perspective view showing the posture of the gantry at the time of lateral imaging by the X-ray imaging apparatus according to this embodiment.

In general, according to one embodiment, a table includes a tabletop on which a subject is placed. A column supports the X-ray tube. A column includes a first sub column, a second sub column, a third sub column, a first connector, and a second connector. The first connector connects the second sub column to the first sub column and includes a first rotation axis parallel to a short axis of the tabletop. The second connector connects the third sub column to the second sub column and includes a second rotation axis perpendicular to the first rotation axis and a central axis of the second sub column. The third sub column supports the X-ray tube.

An X-ray imaging apparatus according to this embodiment will be described below with reference to the accompanying drawings. Note that the same reference numerals denote constituent elements having almost the same functions and arrangements in the following description, and a repetitive description will be made only when required.

FIG. 1 is a view showing the arrangement of an X-ray imaging apparatus according to this embodiment. The X-ray imaging apparatus includes a gantry 1 and a system main body 3. The gantry 1 includes a tabletop 11, a table 12, an X-ray tube 13, a high voltage generator 14, a first housing 16, a column 17, a second housing 18, a base 19, a data acquisition device 20, and mounting portions 28. The system main body 3 includes an input device 31, a system controller 32, an imaging controller 33, an image generator 34, a preprocessor 35, a storage 36, a display processor 37, a display 38, and a mechanism controller 39.

The base 19 holds the table 12 and the column 17. The table 12 includes the tabletop 11. The tabletop 11 is supported so as to be movable vertically and horizontally. The table 12 includes a first moving mechanism for moving the tabletop 11 and a first driving unit which drives the first moving mechanism. A subject is placed on the tabletop 11. The table 12 includes the first housing 16 and the second housing 18. The first housing 16 and the second housing 18 each have a structure which houses an X-ray detector 15 and detachably holds it. The first housing 16 is provided in the table 12 under the tabletop 11. The detection surface of the X-ray detector 15 housed in the first housing 16 faces the X-ray tube at the time of frontal imaging. The second housing 18 is provided on a side of the tabletop 11 on the table 12 which faces the base 19 through the tabletop 11. The detection surface of the X-ray detector 15 housed in the second housing 18 faces the X-ray tube at the time of lateral imaging. The table 12 includes the mounting portions 28 for detachably mounting the second housing 18. The mounting portions 28 are, for example, screw holes for fixing the second housing 18 to the table 12 with fixing screws.

The column 17 is constituted by a first sub column 21, a second sub column 22, a third sub column 23, a first connector 24, and a second connector 25. The first sub column 21 is supported on the base 19 such that the central axis of the first sub column 21 is perpendicular to the surface of the tabletop 11. The first sub column 21 includes a second moving mechanism for moving along a rail 29 provided in the base 19 and a second driving unit which drives the second moving mechanism.

The first connector 24 connects the second sub column 22 to the first sub column 21. The first connector 24 has a first rotating mechanism 26 which rotates the second sub column 22 about a rotation axis R1 relative to the first sub column 21. The rotation axis R1 is a fixed axis parallel to the short axis of the surface of the tabletop 11. A third driving unit drives the first rotating mechanism 26.

The second connector 25 connects the third sub column 23 to the second sub column 22. The second connector 25 has a second rotating mechanism 27 which rotates the third sub column 23 about a rotation axis R2 relative to the second sub column 22. The rotation axis R2 is perpendicular to the rotation axis R1 and the central axis of the second sub column 22. The second sub column 22 can rotate about the rotation axis R1 relative to the first sub column 21. The rotation axis R2 is therefore a variable axis. A fourth driving unit drives the second rotating mechanism 27. The X-ray tube 13 is fixed to the distal end of the third sub column 23.

The first to fourth driving units are, for example, motors. However, the fourth driving unit need not be provided for the X-ray imaging apparatus. In this case, the second rotating mechanism 27 is connected to the first rotating mechanism 26 and rotated. A mechanical arrangement for interlocking the first rotating mechanism 26 with the second rotating mechanism 27 and interlocking operation will be described later.

The X-ray tube 13 is constituted by an X-ray tube and a collimator. The X-ray tube generates X-rays upon reception of a high voltage (tube voltage) from the high voltage generator 14. The X-ray tube has a radiation window for radiating X-rays. The collimator is attached to the radiation window. The collimator has a movable stop. The movable stop adjusts the irradiation field of X-rays emitted from the X-ray tube under the control of the imaging controller 33. The movable stop forms the X-rays emitted from the X-ray tube into, for example, a conical shape or pyramidal shape.

The X-ray detector 15 includes a plurality of X-ray detection elements. The plurality of X-ray detection elements are arranged into a two-dimensional array. A detector in the form of a two-dimensional array is called an FPD (Flat Panel Display). Each element of the FPD detects X-rays emitted from the X-ray tube 13 and transmitted through a subject. Each pixel of the FPD outputs an electrical signal corresponding to a detected X-ray intensity. The X-ray detector 15 is housed in the first housing 16 or the second housing 18 or removed from the first housing 16 or the second housing 18 by the operator in accordance with the imaging posture of the X-ray apparatus. For this operation, the X-ray detector 15 has a mechanism, e.g., a knob, which allows the operator to house and remove in and from the X-ray detector 15 in each housing.

The data acquisition device 20 generates data by performing various types of correction processing, amplification processing, A/D conversion processing, and the like for the electrical signals output from the X-ray tube 13. The input device 31 functions as a man-machine interface with which the operator inputs instructions to the X-ray imaging apparatus. The input device 31 includes a switch for switching between the frontal imaging mode and the lateral imaging mode and a trackball, various types of switches, buttons, mouse, keyboard, foot pedal, and touch panel for inputting, to the apparatus main body, various types of instructions from the operator, an instruction to set an ROI (Region Of Interest), various types of image quality condition setting instructions, instructions to set imaging conditions, and the like.

The system controller 32 is, for example, an integrated circuit such as an ASIC (Application Specific Integrated Circuit) or FPGA (Field Programmable Gate Array) or an electronic circuit such as a CPU (Central Processing Unit) or MPU (Micro Processing Unit). More specifically, the system controller 32 comprehensively controls operation in accordance with instructions from the operator via the input device 31, for example, operation associated with X-ray imaging, operation associated with the movement of mechanisms, and operation associated with image processing.

The mechanism controller 39 decides conditions associated with the moving operation of each mechanism and transmits movement control signals corresponding to conditions to the first and second moving mechanisms and the first and second rotating mechanisms under the control of the system controller 32. The imaging controller 33 decides conditions associated with imaging, e.g., an X-ray tube voltage, tube current, and imaging time and transmits imaging control signals to the high voltage generator 14, the X-ray detector 15, and the data acquisition device 20 under the control of the system controller 32.

The image generator 34 generates a two-dimensional X-ray image based on the data output from the data acquisition device 20 and processed by the preprocessor 35 under the control of the system controller 32. The storage 36 is, for example, a hard disk which stores the data of the two-dimensional X-ray image generated by the image generator 34. The storage 36 also stores various types of items set by the operator via the input device 31, movement conditions at the time of frontal imaging, movement conditions at the time of lateral imaging, and a GUI (Graphical User Interface) for receiving various types of instructions from the operator.

The display processor 37 reads out the GUI, the data of various types of images, and the like from the storage 36 under the control of the system controller 32. The display processor 37 performs processing associated with image browsing for read images, e.g., enlargement/reduction of X-ray images, addition of annotations to X-ray images, smoothing processing of X-ray images, and edge processing and displays the resultant images on the display 38.

Figure 4:
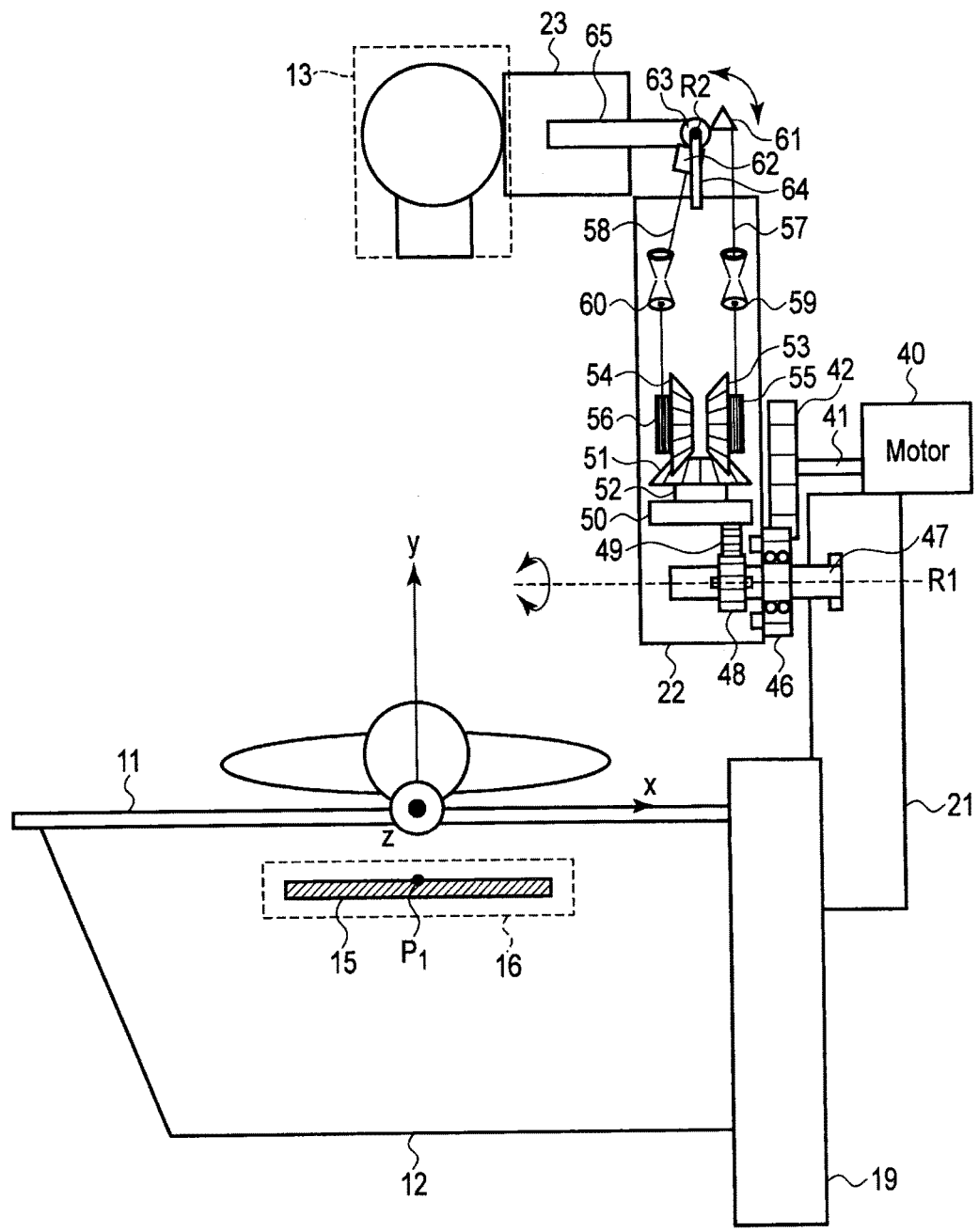
FIG. 4 is a view showing an example of a mechanical arrangement for interlocking a first rotating mechanism 26 with a second rotating mechanism 27.

A mechanical arrangement for interlocking the second rotating mechanism 27 with the first rotating mechanism 26 will be described next with reference to FIG. 4. FIG. 4 is a view showing an example of the mechanical arrangement for interlocking the second rotating mechanism 27 with the first rotating mechanism 26.

A motor 40 mounted on the first sub column 21 is connected to a drive shaft 41. A first gear 42 is fixed to the drive shaft 41. A second gear 46 fixed to the second sub column 22 meshes with the first gear 42. The second gear 46 is supported on a connecting shaft 47 through a bearing. The connecting shaft 47 connects the first sub column 21 to the second sub column 22. One end of the connecting shaft 47 is fixed to the first sub column 21. The other end of the connecting shaft 47 is rotatably supported on the second sub column 22 through a bearing. A third gear 48 is fixed to the connecting shaft 47.

A fourth gear 49 meshes with the third gear 48. A fifth gear 50 in the form of a face gear meshes with the fourth gear 49. The fifth gear 50 is fixed to one end of a fixed shaft 52. A sixth gear 51 in a bevel shape is fixed to the other end of the fixed shaft 52. A pair of a seventh gear 53 and an eighth gear 54, each having the same number of teeth and a bevel shape, mesh with the sixth gear 51 at positions facing each other. A first pulley 55 is fixed to the seventh gear 53. A second pulley 56 is fixed to the eighth gear 54.

A first wire 57 is fixed to the first pulley 55. One end of the first wire 57 is fixed to the first pulley 55. The other end of the first wire 57 is fixed to a first rotating rod 61 through a first tensioner 59. The first tensioner 59 is provided to prevent the first wire 57 from being loosened and guide the first wire 57 to the take-up position of the first pulley 55. A second wire 58 is connected to the second pulley 56. One end of the second wire 58 is fixed to the second pulley 56. The other end of the second wire 58 is fixed to a second rotating rod 62 through a second tensioner 60. The second tensioner 60 is provided to prevent the second wire 58 from being loosened and guide the second wire 58 to the take-up position of the second pulley 56.

The first rotating rod 61 and the second rotating rod 62 are fixed to a rotating mechanism 63. The rotation axis R2 of the rotating mechanism 63 is perpendicular to the rotation axis R1. The rotating mechanism 63 is fixed to the second sub column 22 through a fixed arm 64. A rotating arm 65 is connected to the rotating mechanism 63. The third sub column 23 is fixed to the rotating arm 65. The X-ray tube 13 is fixed to the distal end of the third sub column 23.

The operation of an X-ray imaging apparatus according to this embodiment will be described next. The operation will be described with reference to FIGS. 2 and 3 by exemplifying a procedure until the X-ray imaging apparatus acquires a captured frontal image and a captured lateral image concerning the ROI of a subject. FIG. 2 is a view showing the posture of the gantry at the time of frontal imaging by the X-ray imaging apparatus according to this embodiment. FIG. 3 is a view showing the posture of the gantry at the time of lateral imaging by the X-ray imaging apparatus according to this embodiment.

In the description of this embodiment, coordinates are expressed by the spatial coordinate system of an examination room. More specifically, the x-axis (lateral direction) is parallel to the short axis of the surface of the tabletop 11, the z-axis is parallel to the long axis of the surface of the tabletop 11, and the y-axis (frontal direction) is perpendicular to the surface of the tabletop 11. The origin of the x-y-z coordinate system is set at a reference position, e.g., the central position of the surface of the tabletop 11 when the tabletop 11 is at the lowest position in the range in which the tabletop 11 can move vertically.

In the X-ray imaging apparatus according to this embodiment, the positions of the mounting portions 28 at which the second housing 18 is mounted on the table 12 are adjusted such that the z-coordinate of the center of the detection surface of the X-ray detector 15 housed in the second housing 18 almost coincides with the z-axis of the center of the detection surface of the X-ray detector 15 housed in the first housing 16.

The length of the first sub column 21 and the height of the second housing 18 are adjusted such that the y-coordinate of the center of the detection surface of the X-ray detector 15 housed in the second housing 18 almost coincides with the y-coordinate of the rotation axis R1.

The storage 36 stores frontal imaging movement conditions and lateral imaging movement conditions. The frontal imaging movement conditions are conditions under which the mechanism controller 39 controls the respective driving units when shifting from the posture of the gantry at the time of lateral imaging to the posture of the gantry at the time of frontal imaging. The frontal imaging movement conditions define at least a rotation angle $\theta 1$ of the first rotating mechanism 26, a rotation angle $\phi 1$ of the second rotating mechanism 27, and a movement amount $\Delta Z1$ of the second moving mechanism with reference to the position of the gantry 1 at the time of lateral imaging.

The rotation angle $\theta 1$ and the rotation angle $\phi 1$ are set so as to make the X-ray central line of the X-ray tube 13 perpendicular to the detection surface of the X-ray detector 15 housed in the first housing 16. The movement amount $\Delta Z1$ is set such that the z-coordinate of the position where the X-ray central line of the X-ray tube 13 intersects with the tabletop 11 coincides with the z-axis of the central position of the detection surface of the X-ray detector 15 housed in the first housing 16. Note that the length of the third sub column 23 is adjusted such that the x-coordinate of the position where the X-ray central line of the X-ray tube 13 intersects with the tabletop 11 coincides with the x-coordinate of the central position of the detection surface of the X-ray detector 15 housed in the first housing 16.

Note that the frontal imaging movement conditions may include the tabletop movement amount of the tabletop 11. The tabletop movement amount is the movement amount of the tabletop 11 with which the imaging central position at the time of frontal imaging coincides with the central position of the ROI set at the time of lateral imaging. Letting the frontal imaging movement conditions include the tabletop movement amount can automatically move the tabletop 11 for frontal and lateral imaging of the ROI.

The lateral imaging movement conditions are conditions under which the mechanism controller 39 controls the respective driving units when shifting from the posture of the gantry at the time of frontal imaging to the posture of the gantry at the time of lateral imaging. The lateral imaging movement conditions define a rotation angle $\theta 2$ of the first rotating mechanism 26, a rotation angle $\phi 2$ of the second rotating mechanism 27, and a movement amount $\Delta Z2$ of the second moving mechanism with reference to the position of the gantry 1 at the time of frontal imaging. The rotation angle $\phi 2$ is set so as to make the X-ray central line of the X-ray tube 13 perpendicular to the detection surface of the X-ray detector 15 housed in the second housing 18. The rotation angle $\theta 2$ and the movement amount $\Delta Z2$ are set so as to make the X-ray central line of the X-ray tube 13 pass through the central position of the detection surface of the X-ray detector 15 housed in the second housing 18.

Note that the lateral imaging movement conditions may include the tabletop movement amount of the tabletop 11. The tabletop movement amount is the movement amount of the tabletop 11 with which the imaging central position at the time of lateral imaging coincides with the central position of the ROI set at the time of frontal imaging. Letting the lateral imaging movement conditions include the tabletop movement amount can automatically move the tabletop 11 for frontal and lateral imaging of the ROI.

Frontal imaging concerning an ROI will be described. At the time of frontal imaging, the operator has detached the second housing 18 from the mounting portions 28 on the table 12. The operator then houses the X-ray detector 15 in the first housing 16 provided on the table 12.

First of all, the operator presses the frontal imaging button provided on the input device 31. In response to the pressing of the frontal imaging button, the mechanism controller 39 reads out the frontal imaging movement conditions from the storage 36. The mechanism controller 39 controls the first and second rotating mechanisms 26 and 27 and the second moving mechanism based on the frontal imaging movement conditions. When the respective driving units perform rotating and moving operations under the control of the mechanism controller 39, the imaging central axis is defined by a line connecting the focus of the X-ray tube to a central position P1 of the detection surface of the X-ray detector 15. In this manner, the shift to the posture for frontal imaging is complete.

First of all, a subject is placed on the tabletop 11. The operator moves the tabletop 11 back and forth via the input device 31 until the central position of the ROI of the object overlaps the imaging central axis. The operator then sets X-ray fluoroscopy or X-ray imaging conditions and the like via the input device 31. Upon completing the setting operation, the operator presses the X-ray fluoroscopy button provided on the input device 31. In response to the pressing of the X-ray fluoroscopy button, the apparatus starts X-ray fluoroscopy based on the set fluoroscopy conditions. The apparatus repeatedly acquires X-ray fluoroscopic images. The apparatus stores the acquired X-ray fluoroscopic images in the storage 36 and displays them on the display 38.

The operator moves the tabletop 11 via the input device 31 while seeing the X-ray fluoroscopic images displayed on the display 38, thereby adjusting the position of the object. Upon moving the tabletop 11 until the central position of the ROI coincides with the central position of the display 38, the operator presses the imaging button at a proper timing under X-ray fluoroscopy. The apparatus then performs X-ray imaging with respect to the ROI to acquire a captured X-ray image (X-ray image) concerning the ROI. The storage 36 stores the data of acquired X-ray images. Since the apparatus uses a high dose of pulse X-rays for X-ray imaging, the exposure dose of the object is high. For this reason, the apparatus executes X-ray imaging in response to the operation of the imaging button by the operator at a proper imaging timing set under fluoroscopy using a low dose of continuous X-rays. The operator then operates the input device 31 to terminate the frontal imaging.

Lateral imaging concerning the same ROI will be described next. At the time of lateral imaging, the operator attaches the second housing 18 to the mounting portions 28 on the table 12. The operator removes the X-ray detector 15 from the first housing 16 and houses the X-ray detector 15 in the second housing 18.

First of all, the operator presses the lateral imaging button provided on the input device 31. In response to the pressing of the lateral imaging button, the mechanism controller 39 reads out the lateral imaging movement conditions from the storage 36. The mechanism controller 39 controls the first and second rotating mechanisms 26 and 27 and the second moving mechanism based on the lateral imaging movement conditions. When the respective driving units perform rotating and moving operations under the control of the mechanism controller 39, the imaging central axis is defined by a line connecting the focus of the X-ray tube to a central position P2 of the detection surface of the X-ray detector 15. In this manner, the shift from the posture for frontal imaging to the posture for lateral imaging is complete. Note that the apparatus may automatically perform shift from the posture for frontal imaging to the posture for lateral imaging in response to the housing of the X-ray detector 15 in the second housing 18 by the operator.

The operator then sets X-ray fluoroscopy or X-ray imaging conditions and the like via the input device 31. Upon completing the setting operation, the operator presses the X-ray fluoroscopy button provided on the input device 31. In response to the pressing of the X-ray fluoroscopy button, the apparatus starts X-ray fluoroscopy based on the set fluoroscopy conditions. The apparatus repeatedly acquires X-ray fluoroscopic images. The apparatus stores the acquired X-ray fluoroscopic images in the storage 36 and displays them on the display 38.

The operator moves the tabletop 11 via the input device 31 while seeing the X-ray fluoroscopic images displayed on the display 38, thereby adjusting the position of the object. Upon moving the tabletop 11 until the central position of the ROI coincides with the central position of the display 38, the operator presses the imaging button at a proper timing under X-ray fluoroscopy. The apparatus then performs X-ray imaging with respect to the ROI to acquire a captured X-ray image (X-ray image) concerning the ROI. The storage 36 stores the data of acquired X-ray images. In this manner, the apparatus completes frontal imaging and lateral imaging with respect to the same ROI.

The details of the rotating operation of the rotation axes R1 and R2 will be described next. Rotating operation at the time of shift from the posture of the gantry at the time of frontal imaging to the posture of the gantry at the time of lateral imaging will be described with reference to FIG. 5.

Figure 5:
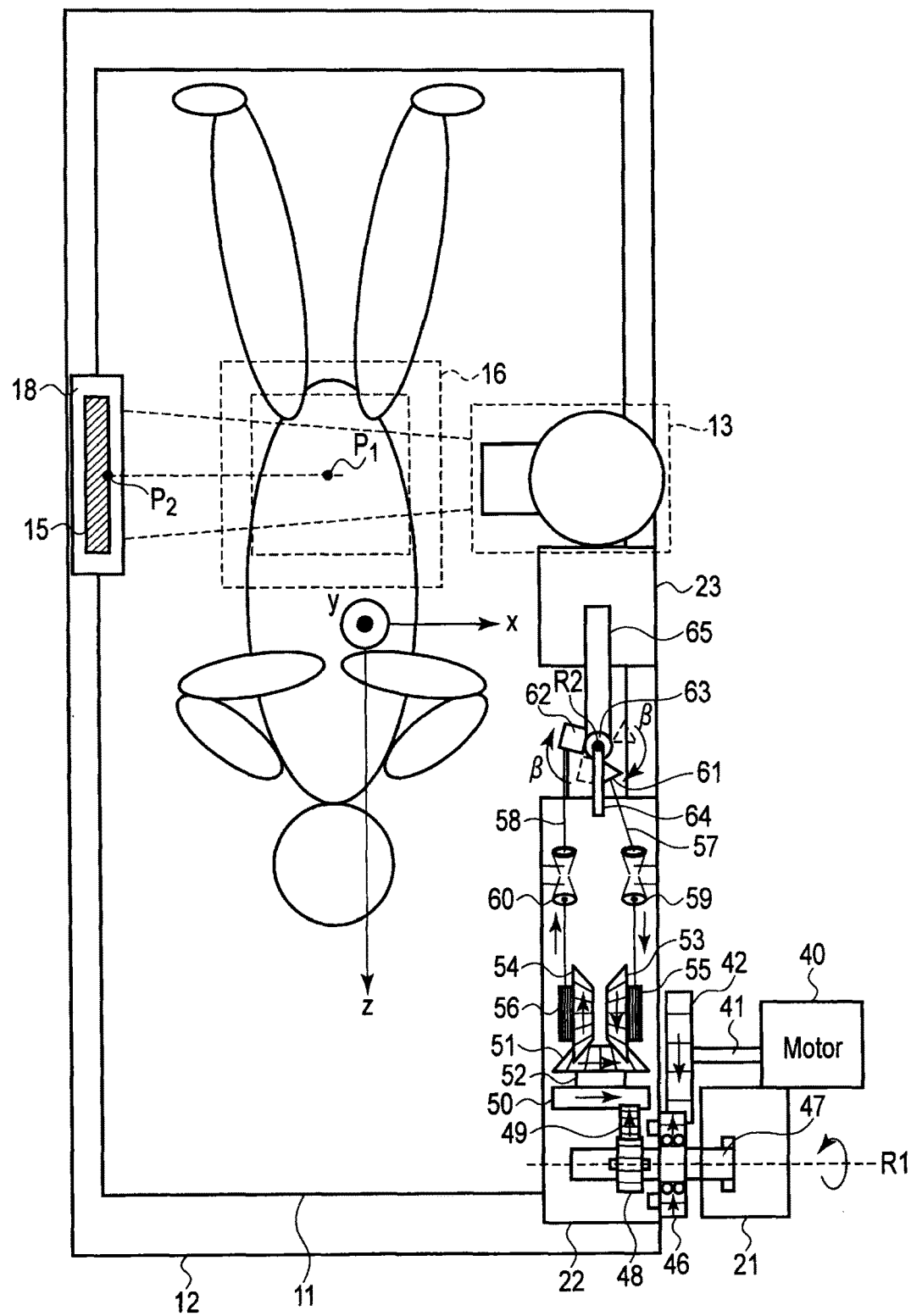
FIG. 5 is a view showing the operating direction of each mechanical portion for shifting from a posture for frontal imaging to a posture for lateral imaging.

FIG. 5 is a view showing the operating direction of each mechanical portion for shifting from the posture of the gantry at the time of frontal imaging to the posture of the gantry at the time of lateral imaging. In the X-ray imaging apparatus according to this embodiment, a wire is fixed to each pulley such that while one pulley takes up a wire, the other pulley feeds the wire.

First of all, the operator presses the lateral imaging button provided on the input device 31. In response to the pressing of the lateral imaging button, the mechanism controller 39 reads out the lateral imaging movement conditions stored in the storage 36. The lateral imaging movement conditions include the rotating direction, rotational speed, and rotation time of the motor 40 which are set to rotate the first rotating mechanism 26 through the angle 42 from the position of the gantry 1 at the time of frontal imaging. The mechanism controller 39 controls the motor 40 based on the lateral imaging movement conditions.

The motor 40 rotates under the lateral imaging movement conditions under the control of the mechanism controller 39. When shifting to the posture of the gantry at the time of lateral imaging, the apparatus rotates the drive shaft 41 and the first gear 42 in the direction indicated by the arrow in FIG. 5. When the first gear 42 rotates, the second gear 46 meshing with the first gear 42 rotates in a direction reverse to the rotating direction of the first gear 42. When the second gear 46 rotates, the second sub column 22 fixed to the second gear 46 rotates about the rotation axis R1 in the direction indicated by the arrow in FIG. 5 together with the second gear 46. The connecting shaft 47 supports the second gear 46 through a bearing, and one end of the connecting shaft 47 is fixed to the first sub column 21, and hence does not rotate. In addition, the third gear 48 fixed to the connecting shaft 47 does not rotate either. Therefore, since the fourth gear 49 meshes with the third gear 48, the fourth gear 49 does not rotate although the third gear 48 rotates. However, the fourth gear 49 is fixed in the second sub column 22, and hence the position of the fourth gear 49 changes as the second sub column 22 rotates. Since this position change occurs at the central position of the third gear 48, the fourth gear 49 rotates relative to the third gear 48.

When the fourth gear 49 rotates, the fifth gear 50 meshing with the fourth gear 49 rotates. The sixth gear 51 is fixed to the fixed shaft 52 together with the fifth gear 50. Therefore, the sixth gear 51 rotates together with the fixed shaft 52 as the fifth gear 50 rotates. As the sixth gear 51 rotates, the seventh gear 53 and the eighth gear 54, which mesh with the sixth gear 51, rotate. The first pulley 55 is fixed to the seventh gear 53. The second pulley 56 is fixed to the eighth gear 54.

The first pulley 55 rotates in the direction indicated by the arrow in FIG. 5 and takes up the first wire 57. As the second pulley 56 rotates in the direction indicated by the arrow in FIG. 5, the second wire 58 is fed by the amount by which the first pulley 55 takes up the first wire 57. As a result, together with the rotating mechanism 63 rotatably supported on the second sub column 22, the first rotating rod 61 of the first rotating rod 61 and the second rotating rod 62 is rotated by the force with which the first pulley 55 takes up the first wire 57. The rotating direction is the β direction in FIG. 5 about the rotation axis R2 with reference to the position at the time of frontal imaging. As the rotating mechanism 63 rotates in the β direction about the rotation axis R2, the rotating arm 65 connected to the rotating mechanism 63 and the third sub column 23 fixed to the rotating arm 65 rotate in the β direction in FIG. 5 about the rotation axis R2 with reference to the position at the time of frontal imaging.

The X-ray tube 13 fixed to the distal end of the third sub column 23 therefore rotates in the β direction about the rotation axis R2. Note that the amount by which the first pulley 55 takes up the first wire 57 and the amount by which the second pulley 56 feeds the second wire 58 are adjusted by the number of teeth and system of each gear so as to rotate the second rotating mechanism 27 through the angle θ2 from the position of the gantry 1 at the time of frontal imaging. Interlocking operation concerning the rotation axes R1 and R2 completes shift from the posture for frontal imaging to the posture for lateral imaging.

The interlocking operation of the first rotating mechanism 26 and second rotating mechanism 27 at shift from the posture for lateral imaging to the posture for frontal imaging will be described next with reference to FIG. 6. FIG. 6 is a view showing the operating direction of each mechanical portion for shifting from the posture for lateral imaging to the posture for frontal imaging.

First of all, the operator presses the frontal imaging button provided on the input device 31. In response to the pressing of the frontal imaging button, the mechanism controller 39 reads out the frontal imaging movement conditions stored in the storage 36. The frontal imaging movement conditions include the rotating direction, rotational speed, and rotation time of the motor 40 which are set to rotate the first rotating mechanism 26 through the angle 41 from the position of the gantry 1 at the time of lateral imaging. More specifically, the rotating direction of the motor 40 based on the frontal imaging movement conditions is reverse to the rotating direction of the motor 40 based on the lateral imaging movement conditions. The mechanism controller 39 controls the motor 40 based on the frontal imaging movement conditions.

Subsequently, the interlocking operation of each gear and each shaft is the same as that at the time of shift from the posture for frontal imaging to the posture for lateral imaging. The motor 40 rotates under the frontal imaging movement conditions under the control of the mechanism controller 39. When shifting to the posture of the gantry at the time of frontal imaging, the apparatus rotates the drive shaft 41 and the first gear 42 in the direction indicated by the arrow in FIG. 6. The second pulley 56 then rotates in the direction indicated by the arrow in FIG. 6 to take up the second wire 58. In addition, the first pulley 55 rotates in the direction indicated by the arrow in FIG. 6 to feed the first wire 57 by the amount by which the second pulley 56 takes up the second wire 58.

As a result, together with the rotating mechanism 63 rotatably supported on the second sub column 22, the second rotating rod 62 of the first rotating rod 61 and the second rotating rod 62 is rotated by the force with which the second pulley 56 takes up the second wire 58. The rotating direction is the α direction in FIG. 6 about the rotation axis R2 with reference to the position at the time of lateral imaging. As the rotating mechanism 63 rotates in the α direction about the rotation axis R2, the rotating arm 65 connected to the rotating mechanism 63 and the third sub column 23 fixed to the rotating arm 65 rotate in the α direction in FIG. 6 about the rotation axis R2 with reference to the position at the time of frontal imaging. Therefore, the X-ray tube 13 fixed to the distal end of the third sub column 23 rotates in the α direction about the rotation axis R2.

Note that the amount by which the first pulley 55 feeds the first wire 57 and the amount by which the second pulley 56 takes up the second wire 58 are adjusted by the number of teeth and diameter of each gear so as to rotate the second rotating mechanism 27 through the angle φ1 from the position of the gantry 1 at the time of lateral imaging. Interlocking operation concerning the rotation axes R1 and R2 completes shift from the posture for lateral imaging to the posture for frontal imaging.

In the above description of the rotating operation of the second rotating mechanism 27 which interlocks with the first rotating mechanism 26, the second rotating mechanism 27 for rotating the X-ray tube 13 rotates as the first pulley 55 or the second pulley 56 takes up the first wire 57 or the second wire 58. The first pulley 55 and the second pulley 56 rotate upon interlocking with the respective gears and the respective shafts. That is, the drive force of the motor 40 is transmitted to each gear and each shaft to shift from the frontal imaging posture to the lateral imaging posture and shift from the lateral imaging posture to the frontal imaging posture. However, it is not necessary to shift to one imaging posture by using the drive force of the motor 40.

The rotating arm 65 connected to the second rotating mechanism 27 may be fixed to the second sub column 22 with an elastic fixing rubber at, for example, the frontal imaging posture instead of the eighth gear 54 and the second pulley 56. Then, as the first pulley 55 takes up the first wire 57, the rotating mechanism 63 rotates to shift from the frontal imaging posture to the lateral imaging posture. At this time, the fixing rubber is set in a stretched state. The force (rubber elastic force) of the fixing rubber for restoration to the initial state at the frontal imaging posture rotates the second rotating mechanism 27 to make shift from the lateral imaging posture to the frontal imaging posture.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An X-ray imaging apparatus comprising:
    a table, which includes a tabletop on which a subject is placed;
    an X-ray tube which generates X-rays;
    an X-ray detector which detects the X-rays; and
    a column which supports the X-ray tube;

wherein the column includes a first sub column, a second sub column rotatably connected to the first sub column at one end portion of the second sub column, and a third sub column rotatably connected to an other end portion of the second sub column;

wherein the first sub column is arranged to extend along a direction perpendicular to a surface of the tabletop;

wherein the third sub column supports the X-ray tube;

wherein the X-ray detector is placed on an opposite side of the table to the X-ray tube to acquire an X-ray image with an arrangement in a lateral imaging posture in which the third sub column and the second sub column are both arranged along a long axis of the tabletop; and wherein the X-ray detector is placed under the tabletop of the table to face the X-ray tube to acquire an X-ray image with an arrangement in a frontal imaging posture in which the third sub column is arranged along a short axis of the tabletop.

2. The X-ray imaging apparatus of claim 1, further comprising an input device which allows an operator to input an instruction to change the arrangement of the X-ray tube, the X-ray detector, and the column between the frontal imaging posture and the lateral imaging posture with respect to the subject;

wherein an axis of the central X-ray of the X-ray tube intersects with the surface of the tabletop at the frontal imaging posture, the axis of the central X-ray of the X-ray tube is parallel to the surface of the tabletop at the lateral imaging posture, and the table includes a first housing and a second housing each detachably housing the X-ray detector;

wherein the first housing is provided at a position facing the X-ray tube in a state of the frontal imaging posture; and, wherein the second housing is provided at a position on the table so as to face the X-ray tube in a state of the lateral imaging posture on the table.

3. The X-ray imaging apparatus of claim 2, wherein the axis of the central X-ray of the X-ray tube at the frontal imaging posture intersects with the axis of the central X-ray of the X-ray tube at the lateral imaging posture.

4. The X-ray imaging apparatus of claim 1, further comprising:

an input device which allows an operator to input an instruction to change the arrangement of the X-ray tube, the X-ray detector, and the column between the frontal imaging posture and the lateral imaging posture with respect to the subject;

a column moving mechanism which moves the first sub column in a long axis direction of the tabletop;

a controller which controls the column moving mechanism;

a first rotating mechanism which rotates the second sub column relative to the first sub column; and, a second rotating mechanism which rotates the third sub column relative to the second sub column; and wherein an axis of the central X-ray of the X-ray tube intersects with the surface of the tabletop at the frontal imaging posture, the axis of the central X-ray of the X-ray tube is parallel to the surface of the tabletop at the lateral imaging posture, and the controller controls the column moving mechanism, together with the first rotating mechanism and the second rotating mechanism, in accordance with an instruction from the input device to change the arrangement of the X-ray tube, the X-ray detector, and the column between the frontal imaging posture from the input device and the lateral imaging posture.

5. The X-ray imaging apparatus of claim 1, further comprising:

a first rotating mechanism which rotates the second sub column about a first rotation axis relative to the first sub column;

a second rotating mechanism which rotates the third sub column about a second rotation axis relative to the second sub column; and, a follower mechanism which makes the first rotating mechanism and the second rotating mechanism rotate synchronously.

6. An X-ray imaging apparatus comprising:

an X-ray tube configured to generate X-rays;

an X-ray detector configured to detect the X-rays;

a table configured to include a tabletop on which a subject is to be placed;

a column provided on one side of the tabletop and configured to support the X-ray tube;

a first housing provided under the tabletop and configured to detachably house the X-ray detector; and a second housing provided on an other side of the tabletop and configured to detachably house the X-ray detector;

wherein the column includes a first sub column, a second sub column rotatably connected to the first sub column at one end portion of the second sub column, and a third sub column rotatably connected to an other end portion of the second sub column;

wherein the first sub column is arranged to extend along a direction perpendicular to a surface of the tabletop; and wherein the third sub column supports the X-ray tube to face the X-ray detector with the third sub column rotated with respect to the second sub column, and the second sub column rotated with respect to the first sub column in accordance with a position of the X-ray detector to capture an image.

7. The X-ray imaging apparatus according to claim 1, wherein the column further includes a first connector and a second connector;

wherein the first connector connects the second sub column to the first sub column, and includes a first rotation axis parallel to a short axis of the tabletop; and wherein the second connector connects the third sub column to the second sub column, and includes a second rotation axis perpendicular to the first rotation axis and to a direction of extension of the second sub column.

8. The X-ray imaging apparatus according to claim 2, wherein the second housing is detachably provided at a position on the table.

9. The X-ray imaging apparatus according to claim 6, wherein the column further includes a first connector and a second connector;

wherein the first connector connects the second sub column to the first sub column, and includes a first rotation axis parallel to a short axis of the tabletop; and wherein the second connector connects the third sub column to the second sub column, and includes a second rotation axis perpendicular to the first rotation axis and to a direction of extension of the second sub column.

* * * * *